United States Patent [19]
Umezawa et al.

[11]  4,170,642
[45]  Oct. 9, 1979

[54] DERIVATIVES OF KANAMYCIN A

[75] Inventors: Hamao; Umezawa; Kenji Maeda, both of Tokyo; Schinichi Kondo, Yokohama; Sumio Umezawa, Tokyo; Osamu Tsuchiya, Yokohama; Shunzo Fukatsu, Tokyo, all of Japan

[73] Assignee: Zaidan Hojin Biseibutsu Kagaku Kenkyu Kai, Tokyo, Japan

[21] Appl. No.: 557,590

[22] Filed: Mar. 12, 1975

Related U.S. Application Data

[63] Continuation-in-part of Ser. No. 402,085, Oct. 1, 1973, Pat. No. 4,001,208.

[30] Foreign Application Priority Data

Mar. 22, 1974 [JP] Japan ................................. 49-31548

[51] Int. Cl.$^2$ ....................... A61K 31/71; C07H 15/22
[52] U.S. Cl. ...................................... 424/180; 536/10; 536/17 R

[58] Field of Search ................... 260/210 AB, 210 K; 536/10

[56] References Cited

U.S. PATENT DOCUMENTS 3,781,268  12/1973  Kawaguchi et al. ......... 260/210 AB
4,001,208  1/1977  Umezawa et al. ..................... 536/10

OTHER PUBLICATIONS

Umezawa et al., "The Journal of Antibiotics", vol. XXV, No. 12, pp. 743-745, 1972.

Primary Examiner—Johnnie R. Brown
Attorney, Agent, or Firm—Haight & Huard

[57] ABSTRACT

Novel derivatives of kanamycin, 1-N-(L-4-amino-2-hydroxy butyryl)-6'-N-alkylkanamycins, have been prepared which possess improved antibacterial activity against gram-positive and gram-negative bacteria including kanamycin-resistant strains.

8 Claims, No Drawings

DERIVATIVES OF KANAMYCIN A

This application is a continuation-in-part of copending, commonly assigned U.S. patent application Ser. No. 402,085 filed Oct. 1, 1973 and now U.S. Pat. No. 4,001,208 issued Jan. 4, 1977.

This invention relates to novel, useful derivatives of kanamycin, 1-N-(L-4-amino-2-hydroxybutyryl)-6'-N-alkylkanamycins and pharmaceutically acceptable acid addition salts thereof and also to processes for the preparation and use of these derivatives.

Kanamycin (by which is meant kanamycin A unless otherwise indicated) is a well known aminoglycosidic antibiotic which has been widely used as a valuable anti-bacterial agent. Unfortunately, some kanamycin-resistant strains have been found out in recent years and hence many efforts have been made to study the resistance mechanism for these kanamycin-resistant strains.

We, H. Umezawa et al, have observed that some strains of gram-negative bacteria carrying R factor Staphylococcus aureus and Pseudomonas aeruginosa isolated from patients are resistant to kanamycin. As a result of closely studying the resistance mechanism, we have found that these resistant strains produce phosphotransferases capable of phosphorylating the 3'-hydroxyl group of kanamycin, a nucleotidyltransferase capable of nucleotidylating the 2''-hydroxyl group of kanamycin or acetyltransferases capable of acetylating the 6'-amino group of kanamycin, these transferases inactivating the kanamycin. On the basis of this discovery, a variety of derivatives of kanamycin have been prepared and tested to study the relationship between their structures and antibacterial activities. We have now succeeded in obtaining novel derivatives of kanamycin which exhibit improved antibacterial activity even against the various bacterial strains resistant to kanamycin.

According to this invention, therefore, there are provided novel compounds, 1-N-(L-4-amino-2-hydroxybutyryl)-6'-N-alkylkanamycins of the general formula:

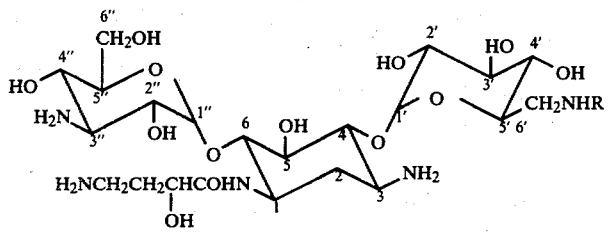

(I)

wherein R is a lower alkyl group, particularly an alkyl group of 1–4 carbon atoms and specifically a methyl or ethyl group, and the pharmaceutically acceptable acid addition salts thereof.

Examples of the pharmaceutically acceptable acid-addition salts of the compounds of the general formula (I) according to this invention include the hydrochloride, sulfate, phosphate, acetate, maleate, fumarate, succinate, tartrate, oxalate, citrate, methanesulfonate, ethanesulfonate, and the like.

The preferred compounds of this invention, 1-N-(L-4-amino-2-hydroxybutyryl)-6'-N-methylkanamycin (hereinafter referred to as 1-AHB-6'-MKM) and 1-N-(L-4-amino-2-hydroxybutyryl)-6'-N-ethylkanamycin (hereinafter referred to as 1-AHB-6'-EKM) have the following characteristics:

The compound 1-AHB-6'-MKM is in the form of white crystalline powder having a decomposition point of 169°–173° C. $[\alpha]_D^{22} = +78°$ (c=1, in water). It corresponds to the empirical formula $C_{23}H_{45}N_5O_{13}$ which has been shown from its elemental analysis. This compound affords a single spot positive to the ninhydrin reaction at Rf=0.13 in thin-layer chromatography (TLC) on silica gel using a mixture of chloroform-methanol-28% aqueous ammonia-water (1:4:2:1 by volume) as a developing solvent.

The compound 1-AHB-6'-EKM is in the form of white crystalline powder having a decomposition point of 184°–188° C. $[\alpha]_D^{25} = +80°$ (c=1, in water). It corresponds to the empirical formula $C_{24}H_{47}N_5O_{13}$ as shown from its elemental analysis. This compound affords a single spot positive to the ninhydrin reaction at Rf=0.20 in TLC on silica gel using the same solvent mixture as above.

The structures of these compounds have been confirmed by n.m.r. spectroscopy and by paper chromatography for the products subjected to hydrolysis in 6 N HCl at 100° C. for 40 minutes.

These two compounds are both of low toxicity, having an $LD_{50}$ value of more than 200 mg/kg when intravenously injected into mice. The compounds at low concentrations can inhibit the growth of various gram-positive and gram-negative bacteria including kanamycin-resistant strains and thus they are effectively used for the treatment of infectious diseases caused by these bacteria.

The minimum inhibitory concentrations (MIC) of 1-AHB-6'-MKM and 1-AHB-6'-EKM against various micro-organisms were determined by the serial dilution method using a nutrient agar medium at 37° C. The results are set out in the Table below.

| | MIC (mcg/ml) | |
|---|---|---|
| Test Microorganisms | 1-AHB-6'-MKM | 1-AMB-6'-EKM |
| Staphylococcus aureus FDA209P | 0.78 | 1.56 |
| Mycobacterium smegmatis ATCC607 | 0.39 | 3.12 |
| Escherichia coli K-12 | 0.39 | 1.56 |
| Escherichia coli K-12 R5 | 0.78 | 1.56 |
| Escherichia coli K-12 ML1629 | 0.78 | 3.12 |
| Escherichia coli K-12 ML1630 | 1.56 | 6.25 |
| Escherichia coli K-12 ML1410 | 1.56 | 3.12 |

-continued

| Test Microorganisms | MIC (mcg/ml) | |
|---|---|---|
| | 1-AHB-6'-MKM | 1-AMB-6'-EKM |
| *Escherichia coli* LA290 R55 | 1.56 | 3.12 |
| *Escherichia coli* LA290 R56 | 0.78 | 1.56 |
| *Escherichia coli* LA290 R64 | 0.78 | 1.56 |
| *Escherichia coli* W677 | 1.56 | 1.56 |
| *Escherichia coli* JR66/W677 | 6.25 | 25 |
| *Klebsiella pneumoniae* PCI 602 | 0.78 | 1.56 |
| *Klebsiella pneumoniae* 22#3038 | 6.25 | 25 |
| *Pseudomonas aeruginosa* A3 | 6.25 | 25 |
| *Pseudomonas aeruginosa* No. 12 | 3.12 | 25 |
| *Pseudomonas aeruginosa* TI-13 | 12.5 | 50 |
| *Pseudomonas aeruginosa* GN315 | 50 | 100 |
| *Pseudomonas aeruginosa* 99 | 12.5 | 100 |

These compounds of this invention are more active than the related compound, 1-N-(L-4-amino-2-hydroxybutyryl) kanamycin which is described in U.S. Pat. No. 3,781,268, against strains producing 6'-N-acetyltransferase, for example *Escherichia coli* K-12 R5 and *Pseudomonas aeruginosa* GN315. It has also been observed that these compounds are not substantially acetylated by a 6'-N-acetyltransferase obtained from *Pseudomonas aeruginosa* GN315. Another related compound, 6'-N-methylkanamycin described in British patent specification No. 1,384,221 does not inhibit kanamycin-resistant strains including *Escherichia coli* K-12 ML1629, K-12 ML1630 and JR66/W677, *Klebsiella pneumoniae* 22#3038, *Pseudomonas aeruginosa* TI-13 and GN315 which produce 3'-phosphotransferases and 2''-nucleotidyl-transferases.

For the treatment of various bacterial infections including many caused by kanamycin-resistant strains, the compounds of this invention may be administered orally or parenterally, for example by intraperitoneal, intravenous, subcutaneous or intramuscular injection.

The compounds are most effective in the treatments of systemic bacterial infections in animals including man when administered parenterally. They are also useful for sterilization of the bowel by oral administration and for surgical sterilization by mechanical cleansing.

When administered subcutaneously at a dosage of more than 2 mg/kg, they have been found to be effective in experimental infections of mice caused by *Staphylococcus aureus* Smith and *Klebsiella pneumoniae* S-1802.

For parenteral administration, they may be used in conventional dosage forms, for example in sterilized aqueous solutions and physiological saline solutions. When parenterally administered to man, the total daily dosage is in the range from 200 mg to 2,000 mg which may be administered in divided form from 2 to 4 times per day.

For oral administration, they may be used in conventional dosage forms known in the art, for example in the forms of powders, capsules, tablets, suppositories, syrups and the like. When orally administered to man, the total daily dosage is in the range from 500 mg to 2,500 mg.

The new compounds of the formula (I) can be prepared according to the process of this invention starting from kanamycin of the structural formula:

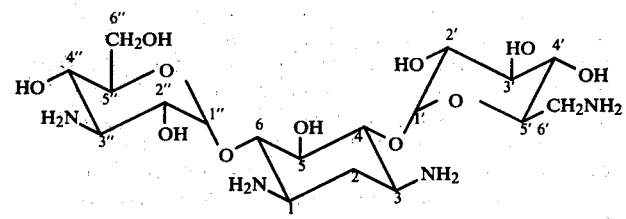

which process comprises acylating the 1-amino group of the kanamycin with L-4-amino-2-hydroxybutyric acid or a functional equivalent thereof and alkylating the 6'-amino group of the kanamycin in a manner known per se.

The acylation may be followed or preceded by the alkylation. The starting kanamycin has four amino groups in its molecule. In order to obtain the desired compounds of the invention, it is required that part or all of the amino groups not to be subjected to the reactions and, if necessary, the hydroxyl groups present in the kanamycin molecule should be previously blocked with protecting groups commonly known in the art.

In an embodiment of the process of this invention, part or all of the three amino groups other than the 1-amino group of kanamycin are blocked with known amino-protecting groups and the blocked derivative thus formed is reacted with L-4-amino-2-hydroxybutyric acid or a corresponding functional equivalent, for example an acid halide, anhydride or active ester, to acylate the 1-amino group. The acylation product is then subjected to 6'-N-alkylation. Alternatively, the process may start from 6'-N-alkylkanamycin previously prepared (see British Patent No. 1,384,221), wherein part or all of the 3- and 3''-amino groups and the 6'-alkylamino group of the alkylkanamycin is (or are) blocked with known amino-protecting group(s) and the blocked derivative is acylated in the same manner as above to form the 1-acylated compound, not followed by the 6'-N-alkylation.

In another embodiment of the present process, part or all of the three amino groups other than the 6'-amino group of kanamycin are blocked with known amino-protecting groups and the blocked derivative thus formed is subjected to 6'-N-alkylation. The alkylation product is then acylated with a 1-N-(L-4-amino-2-hydroxybutyryl)moiety. In an alternative way, starting from 1-N-(L-4-amino-2-hydroxybutyryl) kanamycin previously prepared, one or both of the 3- and 3″-amino groups of the latter is (or are) blocked likewise and the amino-blocked derivative is alkylated to form the 6′-N-alkylation product which need not be subsequently acylated.

In any of the embodiments mentioned above, the amino-protecting groups can be removed from the so obtained product bearing the 1-N-acyl-6′-N-alkyl group in a usual manner known per se to yield the object compound 1-N-(L-4-amino-2-hydroxybutyryl)-6′-N-alkylkanamycin.

In general, suitable examples of the amino-protecting group, their introduction and removal can be found in the review of Y. Wolman in "The Chemistry of the Amino Group" pp. 669–700, Interscience Publishers, 1968 and J. W. Barton in "Protective Groups in Organic Chemistry" pp. 43–94, Plenum Press, 1973.

In a preferred embodiment of the present process, only the 6′-amino group of kanamycin, which is the reactive of the four amino groups, is blocked with a known amino-protecting group and the blocked derivative thus formed is then acylated with an amino-protected derivative of L-4-amino-2-hydroxybutyric acid or a functional equivalent thereof to produce the desired 1-N-monoacylated derivative and the two mono-acylated derivatives as by-products. Without separating these three mono-acylated derivatives (positional isomers) from each other, the remaining free amino groups of each of these derivatives are blocked with amino-protecting groups commonly known in the art but different from that used for blocking the 6′-amino group. Subsequently, only the 6′-amino-protecting group is selectively removed from the derivatives, followed by alkylation to yield the 6′-N-alkylation product from which the remaining amino-protecting groups are then removed. From the reaction mixture comprising the positional isomers thus formed, 1-N-(L-4-amino-2-hydroxybutyryl)-6′-N-alkylkanamycin can be conveniently isolated, for example by a chromatographic technique such as described in more detail hereinafter.

The amino-protecting groups mentioned above for the process of this invention may include those which have been commonly employed in the synthesis of peptides and may be introduced in a conventional manner, although it is preferred to use those amino-protecting groups which will be readily removed eventually with a good reaction yield.

Examples of amino-protecting groups suitable for use in the present process include alkyloxycarbonyl groups such as ethoxycarbonyl, tert-butoxycarbonyl and tert-amyloxycarbonyl; cycloalkyloxycarbonyl groups such as cyclopentyloxycarbonyl and cyclohexyloxycarbonyl; and aralkyloxycarbonyl groups such as benzyloxycarbonyl and p-nitrobenzyloxycarbonyl. A divalent amino-protecting group such as salicylidene may be used to give the blocked derivatives in the form of a Schiff base. It is preferred to use two or more different amino-protecting groups capable of being removed selectively and independently in the course of different reactions.

So far as the protecting group to block the 6′-amino group of kanamycin is concerned, it is most convenient to use the tert-butoxycarbonyl group which is preferentially reactive with to the 6′-amino group and which is readily removable eventually. When the 6′-amino group is to be blocked with a tert-butoxycarbonyl group, for example, kanamycin is dissolved in a mixture of pyridine, water and triethylamine, followed by adding dropwise one or three molar proportions of tert-butoxycarbonyl azide with stirring. The reaction mixture is agitated at room temperature overnight and then concentrated to dryness under reduced pressure. The residue obtained is purified by means of column chromatography using a cation-exchange resin such as "Amberlite" CG50 to give 6′-N-tert-butoxycarbonylkanamycin in a fairly good yield, while the unreacted kanamycin may be recovered for re-use.

In carrying out the process of this invention, L-4-amino-2-hydroxybutyric acid or a function equivalent thereof to be used for acylating the 1-amino group of kanamycin may be preferably in such form that the 4-amino group of the acylating agent has been blocked with a suitable protecting group, which may be any of the amino-protecting groups mentioned above. When the hydroxy-amino acid is to be reacted with 6′-N-tert-butoxycarbonylkanamycin, the amino group of the hydroxy-amino acid is preferably blocked with a protecting group, for example benzyloxycarbonyl, which will not be released upon the removal of the 6′-N-tert-butoxycarbonyl group from said butoxycarbonylkanamycin. The acylation of the 1-amino group of kanamycin with the L-4-amino-2-hydroxybutyryl moiety can be carried out by any known method commonly used in the synthesis of amides. Thus, in a preferred embodiment of the present process where 6′-N-tert-butoxycarbonylkanamycin is initially prepared, the acylating agent may be used preferably in such form that it will be reacted with the 6′-N-tert-butoxycarbonylkanamycin with a high selectivity for the 1-amino group thereof, for example in the form of an active ester of L-4-amino-2-hydroxybutyric acid. The active ester may be formed by any known method, for example by interacting L-4-amino-2-hydroxybutyric acid in which the amino group has been blocked with a benzyloxycarbonyl group with N-hydroxysuccinimide in an anhydrous solvent such as dimethylformamide, acetone or tetrahydrofuran in the presence of a dehydrating agent such as dicyclohexylcarbodiimide. 0.5 or 3 molar proportions of the active ester thus formed may be reacted with 6′-N-tert-butoxycarbonylkanamycin in an aqueous organic solvent such as dimethoxyethane.

The acylation product obtained according to the process of this invention comprises predominantly the desired 1-N-acylated compound and minor proportions of the 3-N-acylated and 3″-N-acylated compounds as by-products. These compounds need not be separated from each other for use in the subsequent step, wherein all the remaining free amino groups present in the acylation product are blocked with suitable amino-protecting groups which will not be released upon the removal of the 6′-N-tert-butoxycarbonyl group, and preferably with the same amino-protecting groups as that used for the blocking of L-4-amino-2-hydroxybutyric acid, for example the benzyloxycarbonyl group. The blocking of amino groups with a benzyloxycarbonyl group may be carried out by any known method and generally by the reaction with benzyloxycarbonyl chloride under basic conditions in water or an aqueous organic solvent.

The benzyloxycarbonylation product thus obtained may be treated with an aqueous solution of trifluoroacetic acid, acetic acid or dilute hydrochloric acid to selectively remove only the 6′-N-tert-butoxycarbonyl group from the product. The resultant product in which the 6′-amino group is blocked no longer is subjected to 6'-N-alkylation to give the desired amino-blocked derivative. The alkylation may be carried out in any known manner commonly used in the art. We prefer to effect the alkylation by interacting the 6'-amino group with an aldehyde having the same number of carbon atoms as the desired alkyl group to be introduced, that is, formaldehyde or a lower alkyl aldehyde such as acetaldehyde, propionaldehyde, butyraldehyde, to convert the amino group into the form of a Schiff base, followed by the normal catalytic reduction or the reduction with sodium borohydride to convert it into a 6'-N-alkylamino group.

The amino-protecting groups in the compound carrying the 1-N-acyl-6'-N-alkyl group which is the final intermediate in the present process can be removed therefrom in a conventional manner. For instance, when the amino-protecting group is the benzyloxycarbonyl group, it may be readily removed by a common technique of by catalytic reduction or treatment with hydrogen bromide-acetic acid. According to a preferred embodiment of the present process, where the 6'-amino group is reacted with an aldehyde to form a Schiff base which is then reduced to effect the alkylation (to form a corresponding alkylamino group) as already mentioned hereinbefore, this reduction may be carried out in a catalytic manner using Pd-C or Pt-C, whereby the introduction of the alkyl group and the removal of the benzyloxycarbonyl group can be achieved simultaneously.

The reaction product obtained by the removal of the remaining amino-protecting groups comprises the object 6'-N-alkyl-N-acyl compound and its positional isomers including the 3-N-acyl and 3''-N-acyl compounds. The object compound may be isolated from the reaction product including the isomers by means of column chromatography using, for example, a weakly acidic cation-exchange resin such as "Amberlite" IRC50 and CG50 (manufactured by Rohm & Haas Co., U.S.A.) and "CM-Sephadex" C-25 -(manufactured by Pharmacia Co., Sweden). The eluate from the chromatographic column with aqueous ammonia is collected in fractions each of a small volume and each of the fractions is tested for its antibacterial activity. The object compound can be recovered from the combined fractions showing a higher antibacterial activity to a resistant strain in a usual manner known in the art.

This invention is further illustrated by, but not limited to, the following Examples.

EXAMPLE 1

Preparation of 1-N-(L-4-amino-2-hydroxybutyryl)-6'-N-methylkanamycin (a) 6'-N-tert-butoxycarbonylkanamycin 20 g (41.3 millimoles) of kanamycin was dissolved in 1,600 ml of a mixture of pyridine-water-triethylamine (10:10:1 by volume), to which was then added 5.9 g (41.3 millimoles) of tert-butoxycarbonyl azide. The reaction mixture was stirred at room temperature for 20 hours and then concentrated to dryness under reduced pressure. The residual solid was dissolved in water and the aqueous solution was passed through a column of 1,000 ml of a cation-exchange resin consisting essentially of methacrylic acid/divinylbenzene copolymer (commercially available as "Amberlite" CG50) to adsorb the butoxycarbonylation products on the resin. The column was then washed with 5,000 ml of water and 5,000 ml of 0.05 N aqueous ammonia, followed by elution with 3,000 ml of 0.1 N aqueous ammonia. Those fractions of the eluate which were positive to the ninhydrin reaction and to the Rydon-Smith reaction and which gave a single spot in a high-voltage paper electrophoresis were combined together and concentrated to dryness, yielding 10.9 g of 6'-N-tert-butoxycarbonylkanamycin as a white powder with a decomposition point of 202°–203° C. Yield: 45.3%. Further elution with 0.3 N aqueous ammonia gave 7.3 g of unreacted kanamycin. Recovery: 36.6%.

(b) Tri-N-benzyloxycarbonyl-mono-N-(L-4-amino-2-hydroxybutyryl) kanamycin 1.754 g (3 millimoles) of 6'-N-tert-butoxycarbonylkanamycin prepared as above was dissolved in a mixture of 12.5 ml of water and 12.5 ml of dimethoxyethane, to which was then added a solution of 1.156 g (3.3 millimoles) of N-hydroxysuccinimide ester of L-4-benzyloxycarbonylamido-2-hydroxybutyric acid in 25 ml of dimethoxyethane. The reaction mixture was stirred for 24 hours at room temperature and then concentrated to dryness under reduced pressure. The resulting condensation product was dissolved, without purification, in a mixture of 12.5 ml of water and 12.5 ml of acetone, to which 1 g (11.9 millimoles) of sodium bicarbonate was added. The mixture was stirred with ice-cooling while 1.68 g (9.9 millimoles) of benzyloxycarbonyl chloride was added dropwise. Thereafter, the mixture was stirred with ice-cooling for 1 hour and at room temperature for a further 18 hours. The resultant white precipitate was filtered off and washed with water to give 3.0 g of the benzyloxycarbonylation product as a white powder. This product was dissolved in 75 ml of 90% trifluoroacetic acid and the solution allowed to stand at room temperature for 1 hour to remove the tert-butoxycarbonyl group from the product. The solution was then concentrated, to which 50 ml of ethyl ether was added to effect the precipitation. The precipitate was filtered off and washed with ethyl ether to give 2.87 g of tri-N-benzyloxycarbonyl-mono-N-(L-4-amino-2-hydroxybutyryl) kanamycin as white powder.

(c) 1-N-(L-4-amino-2-hydroxybutyryl)-6'-N-methylkanamycin 575 mg of tri-N-benzyloxycarbonyl-mono-N-(L-4-amino-2-hydroxybutyryl) kanamycin prepared in step (b) above was dissolved in 8 ml of methanol. To the solution were added 1 ml of 1 N aqueous sodium hydroxide solution and 0.25 ml of 37% aqueous formaldehyde solution. Ten minutes later, 222 mg of sodium borohydride was added and the mixture was allowed to stand overnight at room temperature and then concentrated to dryness. 7 ml of water was added to the residue and the resulting white precipitate filtered off and washed with water to obtain 675 mg of white powder. The latter was dissolved in a mixture of 5 ml of acetic acid, 4 ml of methanol and 1 ml of water. Gaseous hydrogen was passed into the solution at room temperature for 4.5 hours in the presence of a catalyst composed of 300 mg of 5% Pd on carbon to effect the catalytic reduction. The catalyst was filtered off and washed with water. The combined filrate and washing was evaporated to dryness. The residue thus obtained was dissolved in 7 ml of water and the solution adjusted with aqueous ammonia to pH 8.8–9.0 and then passed through a column of 30 ml of "Amberlite CG-50" (ammonium form). The column was washed with 200 ml of water and 150 ml of 0.3 N aqueous ammonia and then eluted with 150 ml of 0.5 N aqueous ammonia. The eluate was collected in 3 ml fractions and each of the fractions was tested according to a usual plate assay method for its anti-bacterial activity to the kanamycin-sensitive strain *Bacillus subtilis* PCI 219 and the kanamycin-resistant strain *Escherichia coil* JR66/W677. Those fractions (39 ml) which showed a higher antibacterial activity to said strains were combined together and concentrated to dryness to give 53 mg of 1-N-(L-4-amino-2-hydroxybutyryl)-6'-N-methylkanamycin in the form of a white powder. Decomposition point: 169°–173° C. Yield: 15% (based on 6'-N-tert-butoxycarbonylkanamycin).

EXAMPLE 2

Preparation of 1-N-(L-4-amino-2-hydroxybutyryl)-6'-N-ethylkanamycin 1.13 g of tri-N-benzyloxycarbonyl)-mono-N-(L-4-amino-2-hydroxybutyryl)kanamycin prepared as in Example 1 (b) was dissolved in 16 ml of methanol, to which were then added 1.8 ml of 2 N aqueous sodium hydroxide solution and 0.74 ml of 90% aqueous acetaldehyde solution. Ten minutes later, 444 mg of sodium borohydride was added and the mixture allowed to stand at room temperature overnight. The reaction solution was then concentrated to dryness, followed by addition of 25 ml of water. The resulting white precipitate was filtered off and washed with water to give 804 mg of white powder. The powder thus obtained was dissolved in a mixture of 6 ml of acetic acid, 4.8 ml of methanol and 1.2 ml of water. Gaseous hydrogen was passed into the solution at room temperature for 6.5 hours in the presence of 400 mg of 5% Pd on carbon as catalyst to effect the catalytic reduction. The catalyst was then filtered off and washed with water. The combined filtrate and washing was evaporated to dryness and the residue dissolved in 12 ml of water. The solution was adjusted with aqueous ammonia to pH 9.2 and passed through a column of 80 ml of "Amberlite CG-50" (ammonium form). The resin in the column was washed with 435 ml of water and 384 ml of 0.3 N aqueous ammonia and then eluted with 384 ml of 0.5 N aqueous ammonia. The eluate was collected in 8 ml fractions and tested in the same manner as in Example 1

(c). The active fractions (56 ml) were combined together and concentrated to dryness to yield 92 mg of 1-N-(L-4-amino-2-hydroxybutyryl)-6'-N-ethylkanamycin in the form of a white powder. Decomposition point: 184°–188° C. Yield: 13% (based on 6'-N-tert-butoxycarbonylkanamycin).

What we claim is:

1. 1-N-(L-4-amino-2-hydroxybutyryl)-6'-N-alkylkanamycin having the formula:

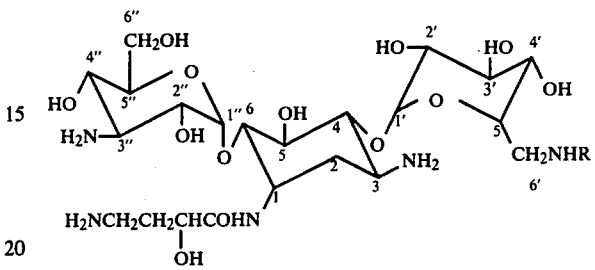

wherein R is methyl or ethyl, and the pharmaceutically acceptable acid addition salt thereof.

2. A compound according to claim 1 in which R is methyl.

3. A compound according to claim 1 in which R is ethyl.

4. A pharmaceutical composition suitable for use in treating susceptible bacterial infections in a living animal comprising a therapeutically effective amount of a compound according to claim 1 in combination with a pharmaceutically acceptable carrier.

5. A process for therapeutically treating bacterial infections in living animals, which comprises administering a therapeutically effective amount of a compound according to claim 1 to an animal affected with a susceptible bacterial infection.

6. Tri-N-benzyloxycarbonyl-mono-N-(L-4-amino-2-hydroxybutyryl) kanamycin.

7. 1-N-(L-4-amino-2-hydroxybutyryl)-6'-N-methylkanamycin A.

8. 1-N-(L-4-amino-2-hydroxybutyryl)-6'-N-ethylkanamycin A.

* * * * *